United States Patent
Parker et al.

(10) Patent No.: US 8,406,888 B2
(45) Date of Patent: Mar. 26, 2013

(54) IMPLANTABLE COCHLEAR ACCESS DEVICE

(75) Inventors: John Parker, Roseville (AU); Herbert Bächler, Meillen (CH); Markus Haller, Yeus (CH)

(73) Assignee: Cochlear Limited, Macquarie University, NSW (AU)

(*) Notice: Subject to any disclaimer, the term of this patent is extended or adjusted under 35 U.S.C. 154(b) by 515 days.

(21) Appl. No.: 12/348,783

(22) Filed: Jan. 5, 2009

(65) Prior Publication Data

US 2009/0306744 A1 Dec. 10, 2009

Related U.S. Application Data

(60) Provisional application No. 61/041,185, filed on Mar. 31, 2008.

(51) Int. Cl.
*A61N 1/375* (2006.01)
(52) U.S. Cl. .................................................. 607/57
(58) Field of Classification Search ............... None
See application file for complete search history.

(56) References Cited

U.S. PATENT DOCUMENTS

| | | | |
|---|---|---|---|
| 5,176,620 A * | 1/1993 | Gilman ........................ | 600/25 |
| 6,402,682 B1 | 6/2002 | Johansson | |
| 6,879,695 B2 | 4/2005 | Maltan et al. | |
| 2008/0082141 A1 * | 4/2008 | Risi ............................. | 607/57 |
| 2009/0306457 A1 * | 12/2009 | Parker et al. ................. | 600/25 |

* cited by examiner

*Primary Examiner* — Kennedy Schaetzle
(74) *Attorney, Agent, or Firm* — Kilpatrick, Townsend & Stockton, LLP.

(57) ABSTRACT

An elongate hollow device for providing direct access to the cochlea of a recipient. The device has a symmetrical shape about a longitudinal axis through the center of the device, and comprises a first end having an aperture with its geometric center positioned at the longitudinal axis, and a distal end having an aperture with its geometric center positioned at the longitudinal axis, wherein the access device is configured to be at least partially positioned in the mastoid bone of the recipient such that the first end is positioned adjacent the surface of the mastoid bone, and the distal end is inserted into the cochlea.

13 Claims, 8 Drawing Sheets

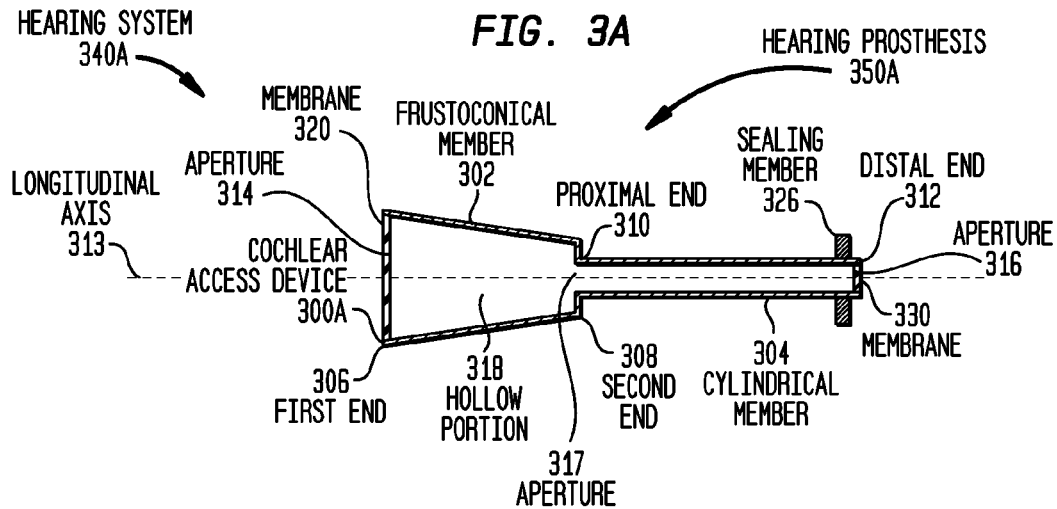
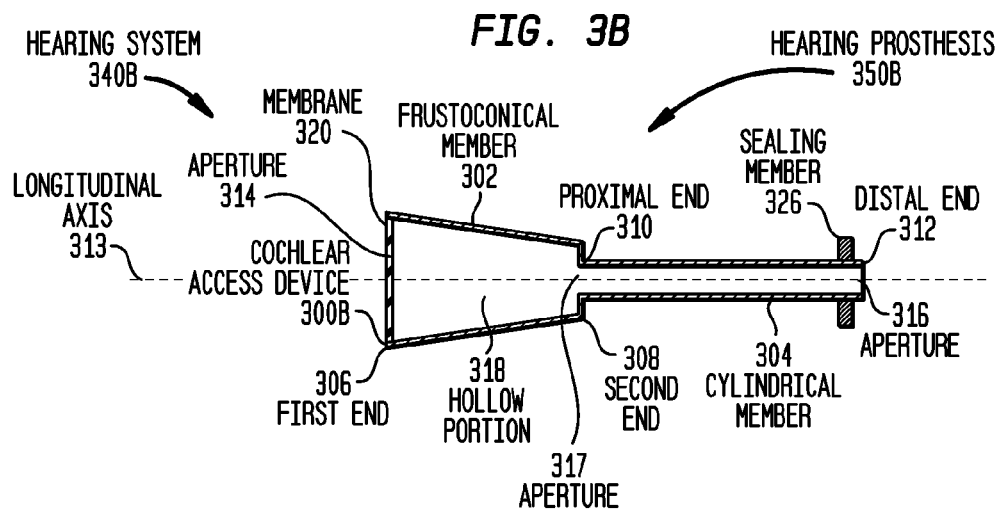
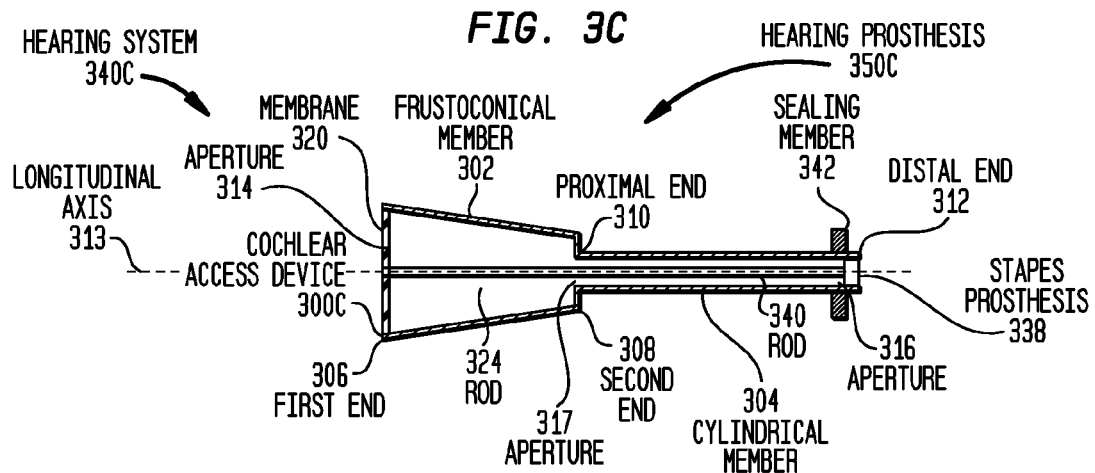

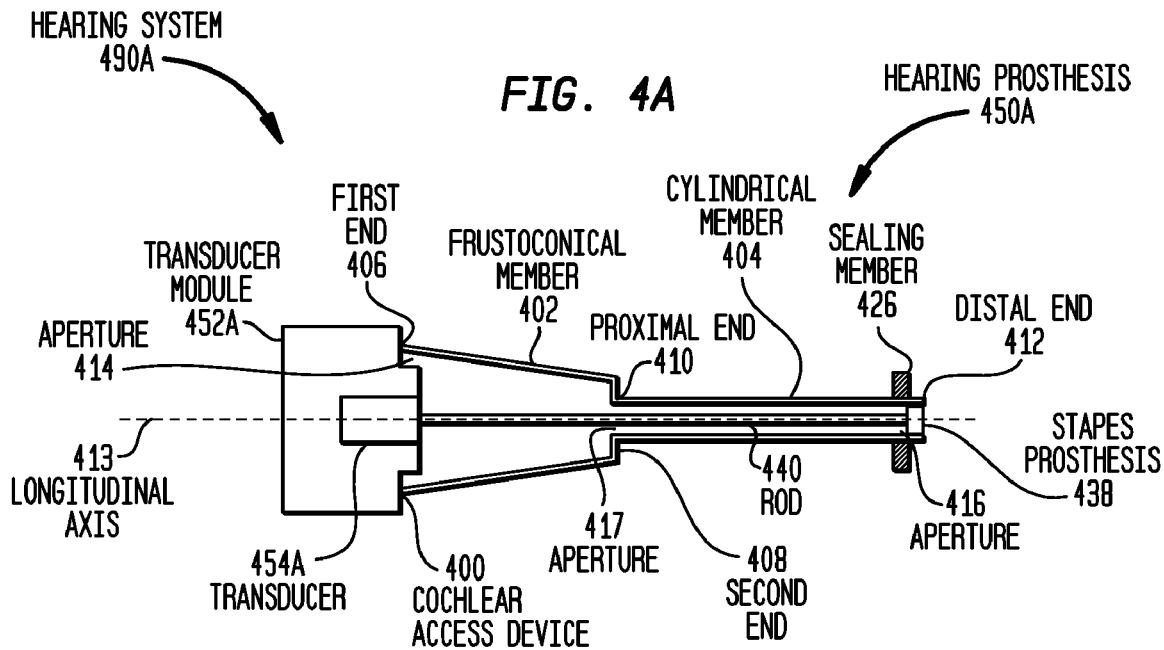
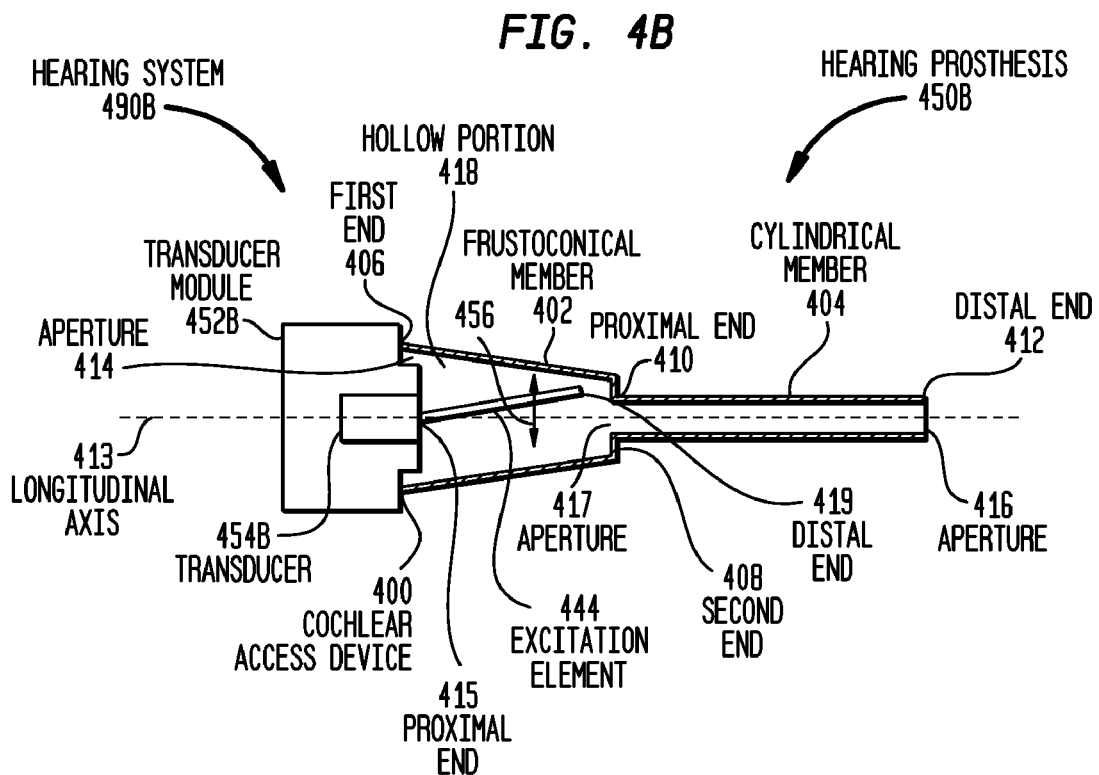

IMPLANTABLE COCHLEAR ACCESS DEVICE

CROSS-REFERENCE TO RELATED APPLICATIONS

The present application claims the benefit of U.S. Provisional Patent Application 61/041,185; filed Mar. 31, 2008, which is hereby incorporated by reference herein. Furthermore, this application is a related to commonly owned and co-pending U.S. patent application entitled "IMPLANTABLE HEARING SYSTEM," filed Jan. 5, 2009 and assigned U.S. patent application Ser. No. 12/348,795. This application is hereby incorporated by reference herein.

BACKGROUND

1. Field of the Invention

The present invention is generally directed to implantable devices, and more particularly, to an implantable cochlear access device.

2. Related Art

Hearing loss, which may be due to many different causes, is generally of two types, conductive and sensorineural. In some cases, an individual may have hearing loss of both types. In many people who are profoundly deaf, however, the reason for their deafness is sensorineural hearing loss. Sensorineural hearing loss occurs when there is damage to the inner ear, or to the nerve pathways from the inner ear to the brain. As such, those suffering from sensorineural hearing loss are thus unable to derive suitable benefit from conventional acoustic hearing aid. As a result, hearing prostheses that deliver electrical stimulation to nerve cells of the recipient's auditory system have been developed to provide persons having sensorineural hearing loss with the ability to perceive sound. Such electrically-stimulating hearing prostheses deliver electrical stimulation to nerve cells of the recipient's auditory system.

As used herein, the recipient's auditory system includes all sensory system components used to perceive a sound signal, such as hearing sensation receptors, neural pathways, including the auditory nerve and spiral ganglion, and parts of the brain used to sense sounds. Electrically-stimulating hearing prostheses include, for example, auditory brain stimulators and cochlear™ prostheses (commonly referred to as cochlear™ prosthetic devices, cochlear™ implants, cochlear™ devices, and the like; simply "cochlear implants" herein.)

Most sensorineural hearing loss is due to the absence or destruction of the cochlea hair cells which transduce acoustic signals into nerve impulses. It is for this purpose that cochlear implants have been developed. Cochlear implants use direct electrical stimulation of auditory nerve cells to bypass absent or defective hair cells that normally transduce acoustic vibrations into neural activity. Such devices generally use an electrode array implanted in the cochlea so that the electrodes may differentially activate auditory neurons that normally encode differential pitches of sound.

Auditory brain stimulators are used to treat a smaller number of recipients with bilateral degeneration of the auditory nerve. For such recipients, the auditory brain stimulator provides stimulation of the cochlear nucleus in the brainstem, typically with a planar electrode array; that is, an electrode array in which the electrode contacts are disposed on a two dimensional surface that can be positioned proximal to the brainstem.

In contrast to sensorineural hearing loss which results from damage to the inner ear, conductive hearing loss occurs when the normal mechanical pathways used to provide sound to hair cells in the cochlea are impeded, for example, by damage to the ossicular chain or to the ear canal. Individuals who suffer from conductive hearing loss typically have some form of residual hearing because the hair cells in the cochlea are undamaged. Such individuals are typically not candidates for a cochlear implant due to the irreversible nature of the cochlear implant. Specifically, insertion of the electrode array into a recipient's cochlea exposes the recipient to the risk of destruction of the majority of the hair cells within the cochlea, resulting in the loss of all residual hearing by the recipient.

As a result, individuals suffering from conductive hearing loss typically receive an acoustic hearing aid. Unfortunately, not all individuals who suffer from conductive hearing loss are able to derive suitable benefit from hearing aids. For example, some individuals are prone to chronic inflammation or infection of the ear canal and cannot wear hearing aids. Similarly, hearing aids are typically unsuitable for individuals who have malformed, damaged or absent outer ears, ear canals and/or ossicular chains.

Those individuals who suffer conductive hearing loss, but cannot derive suitable benefit from hearing aids may benefit from devices which simulate natural hearing by generating mechanical motion of the cochlear fluid (perilymph) without the need for operable outer and middle ears. Some such devices, sometimes referred to mechanical stimulators herein, have one or more components in direct contact with the perilymph so that a propagating wave may be generated within the perilymph. The propagating wave excites the cochlea hair cells and thereby evokes a hearing percept.

SUMMARY

In one aspect of the present invention, an elongate hollow device for providing direct access to the cochlea of a recipient, the device having a symmetrical shape about a longitudinal axis through the center of the device. The device comprises a first end having an aperture with its geometric center positioned at the longitudinal axis, and a distal end having an aperture with its geometric center positioned at the longitudinal axis, wherein the access device is configured to be at least partially positioned in the mastoid bone of the recipient such that the first end is positioned adjacent the surface of the mastoid bone, and the distal end is inserted into the cochlea.

In another aspect of the present invention, a system for rehabilitating the hearing of a recipient is provided. The system comprises an elongate hollow access device having a first end and a distal end, and configured to be at least partially positioned in the mastoid bone of the recipient, such that the first end is positioned adjacent the surface of the mastoid bone, and the distal end is inserted into the cochlea; and a hearing prosthesis configured to be at least partially implanted in the access device and configured to at least one of mechanically and electrically stimulate the recipient's cochlea.

BRIEF DESCRIPTION OF THE FIGURES

Illustrative embodiments of the present invention are described herein with reference to the accompanying drawings, in which:

FIG. 3A is a cross-sectional view of an implantable hearing system, in accordance with embodiments of the present invention;

FIG. 3B is a cross-sectional view of an implantable hearing system, in accordance with embodiments of the present invention;

FIG. 3C is a cross-sectional view of an implantable hearing system, in accordance with embodiments of the present invention;

FIG. 4A is a cross-sectional view of an implantable hearing system, in accordance with embodiments of the present invention;

FIG. 4B is a cross-sectional view of an implantable hearing system, in accordance with embodiments of the present invention;

DETAILED DESCRIPTION

Aspects of the present invention are generally directed to an implantable device that provides direct access to a recipient's cochlea. The cochlear access device comprises a hollow structure that, when implanted, has one end that resides inside the mastoid bone below the recipient's skin, and another end that is directly inserted into the cochlea.

In embodiments of the present invention, the cochlear access device operates as a component of an implantable hearing system. In such embodiments, the cochlear access device is dimensioned to receive hearing prosthesis components so that the components may be implanted in the recipient without destroying elements of a recipient's outer, middle and/or inner ears. The implantable hearing system which includes the cochlear access device may be configured to mechanically and/or electrically stimulate the recipient's cochlea.

Because the cochlear access device provides a direct path to the recipient's cochlea through the mastoid bone, the components of the hearing prosthesis may be implanted without damaging the recipient's outer, middle or inner ear. Similarly, because the components are retained with cochlear access device, implantation and/or replacement of the components is simplified because a surgeon does not need to work around any delicate ear structures.

Figure 1:
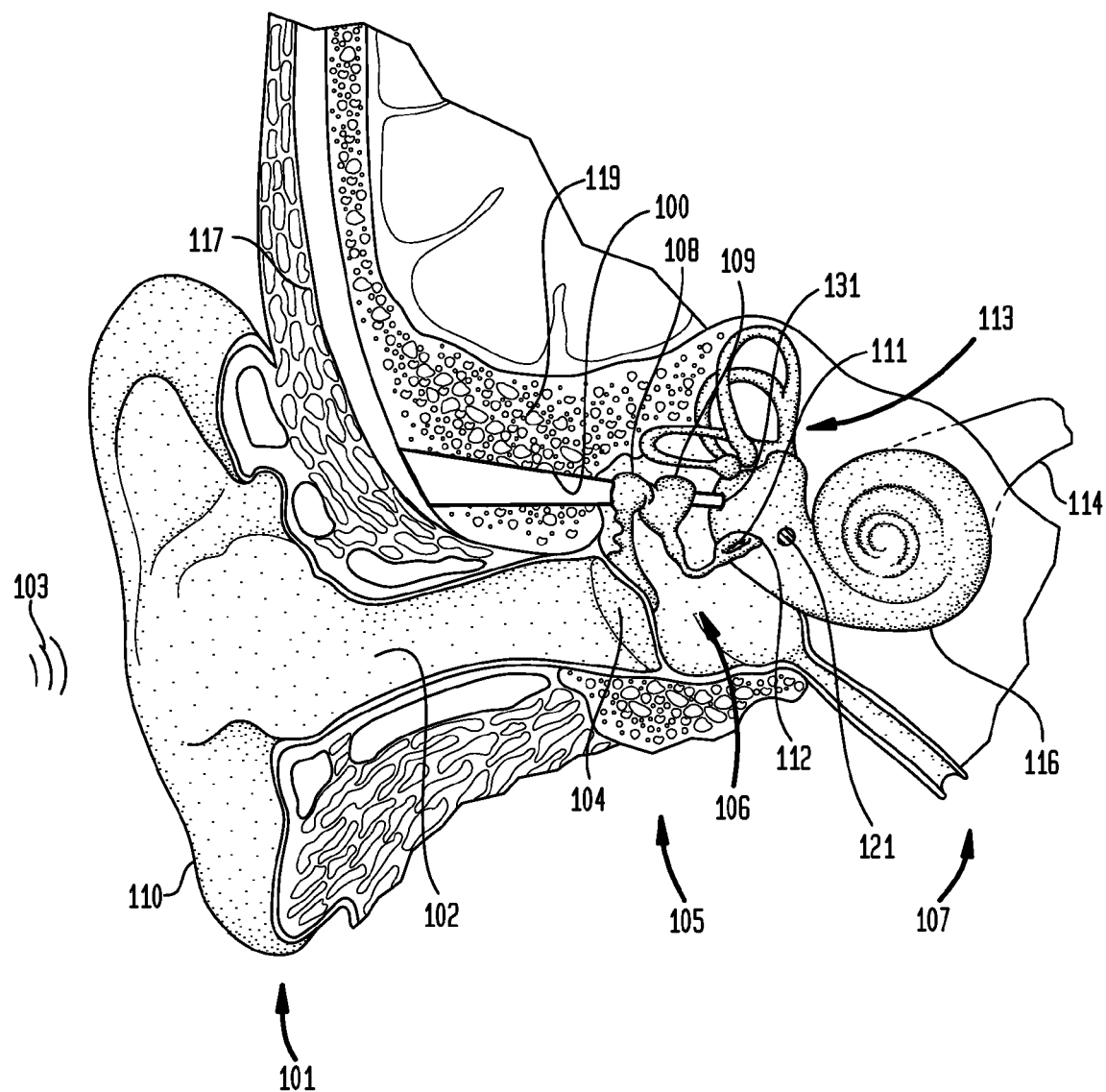
FIG. 1 is a perspective view of a cochlear access device positioned in a recipient in accordance with embodiments of the present invention.

FIG. 1 is a partially-cut way view of a recipient's head illustrating the location of a cochlear access device 100 in accordance with embodiments of the present invention. The relevant components of the recipient's outer ear 101, middle ear 105 and inner ear 107 are described next below, followed by a description of cochlear access device 100.

In a fully functional ear, outer ear 101 comprises an auricle 110 and an ear canal 102. An acoustic pressure or sound wave 103 is collected by auricle 110 and channeled into and through ear canal 102. Disposed across the distal end of ear cannel 102 is a tympanic membrane 104 which vibrates in response to sound wave 103. This vibration is coupled to oval window or fenestra ovalis 112 through three bones of middle ear 105, collectively referred to as the ossicles 106 and comprising the malleus 108, the incus 109 and the stapes 111. Bones 108, 109 and 111 of middle ear 105 serve to filter and amplify sound wave 103, causing oval window 112 to articulate, or vibrate in response to vibration of tympanic membrane 104. This vibration sets up waves of fluid motion of the fluid (perilymph) within cochlea 116. Such fluid motion, in turn, activates tiny hair cells (not shown) inside of cochlea 116. Activation of the hair cells causes appropriate nerve impulses to be generated and transferred through the spiral ganglion cells (not shown) and auditory nerve 114 to the brain (also not shown) where they are perceived as sound.

However, as noted above, various causes may result in the inability of an individual to naturally process sound wave 103 in the manner described above. For example, sensorineural hearing loss occurs when there is damage to inner ear 107, or to the nerve pathways, such as auditory nerve 116, from inner ear 107 to the brain (not shown). Hearing prostheses such as auditory brain stimulators and cochlear™ prostheses (commonly referred to as cochlear™ prosthetic devices, cochlear™ implants, cochlear™ devices, and the like; simply "cochlear implants" herein.) have been developed to provide persons having sensorineural hearing loss with the ability to perceive sound. Cochlear implants use direct electrical stimulation of auditory nerve cells to bypass absent or defective cochlea hair cells (not shown) that normally transduce acoustic vibrations into neural activity. Such devices generally use an electrode array (not shown) implanted into the scala tympani of cochlea 116 so that the electrodes may differentially activate auditory neurons that normally encode differential pitches of sound.

In other individuals, the inability to naturally process sound results from conductive hearing loss. Conductive hearing loss occurs when, the normal mechanical pathways used to provide sound wave 103 to hair cells in cochlea 116 are impeded. Individuals who suffer from conductive hearing loss typically have some form of residual hearing because the hair cells in cochlea 116 are undamaged. Because such individuals are typically not candidates for a cochlear implant due to the irreversible nature of the cochlear implant, individuals suffering from conductive hearing loss typically receive an acoustic hearing aid.

Unfortunately, similar to individuals suffering from sensorineural hearing loss, not all individuals who suffer from conductive hearing loss are able to derive suitable benefit from hearing aids. Such individuals may benefit from devices which simulate natural hearing by generating mechanical motion of the cochlear fluid without the need for an operable outer and/or middle ear. Some such devices, sometimes referred to mechanical stimulators herein, have one or more components in direct contact with the perilymph so that a propagating wave may be generated within the cochlea. The propagating wave excites the cochlea hair cells and thereby evokies a hearing percept.

As discussed in greater detail below, a cochlear access device in accordance with embodiments of the present invention may comprise an element of an implantable hearing system which mechanically electrical stimulates the recipient's inner ear. For example, as discussed in greater detail below, a cochlear access device may comprise an element of a hearing system which includes a cochlear implant or other devices that mechanically generate motion of the cochlear perilymph.

FIG. 1 illustrates the position of an exemplary cochlear access device 100 following implantation of the device into a recipient. As shown, cochlear access device 100 extends through mastoid bone 119 behind ossicles 106. One end (not shown) of cochlear access device 100 is below skin 117 of the recipient, while a distal end 131 is inserted into cochlea 116. Distal end 131 may inserted into cochlea 116 in at variety of locations, such as through oval window 112, round window 121, a cochleostomy in cochlea 116 near semicircular canals 113 or another location. Details of a cochlear access device, such as cochlear access device 100, are provided below with reference to FIGS. 2A-2B.

Figure 2A:
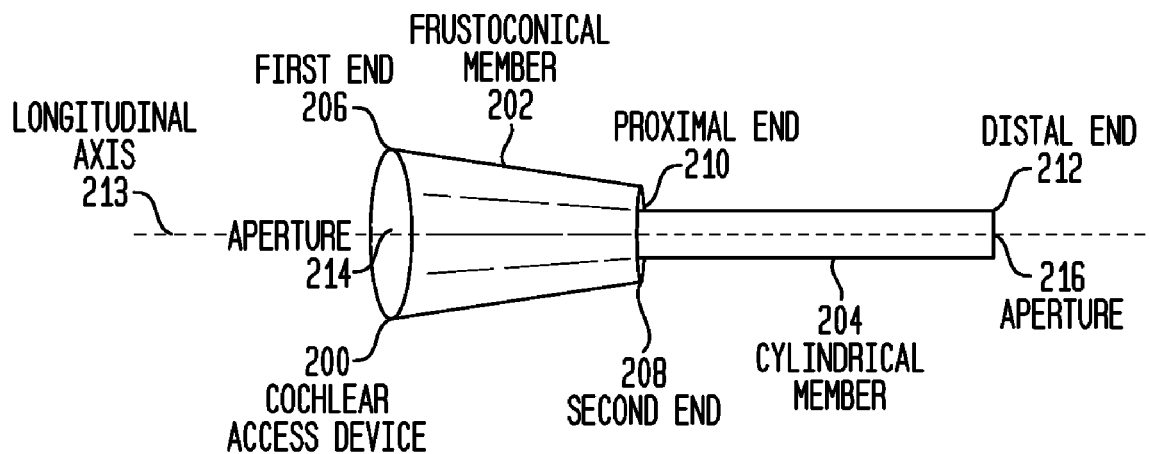
FIG. 2A is a perspective view of a cochlear access device in accordance with embodiments of the present invention.
Figure 2B:
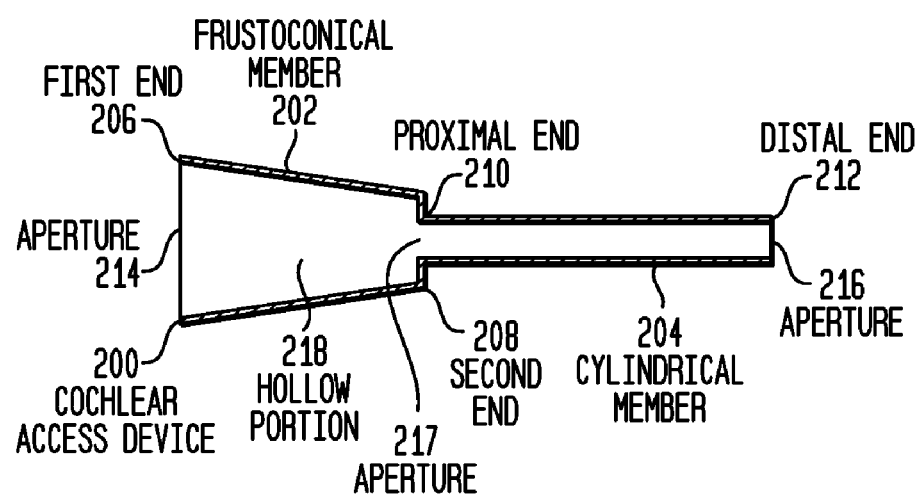
FIG. 2B is a cross-sectional view of the cochlear access device of FIG. 2A.

FIGS. 2A and 2B illustrate one embodiment of cochlear access device 100, referred to as cochlear access device 200. FIG. 2A provides a perspective view of cochlear access device 200, while FIG. 2B provides a cross-sectional view of the device. In the illustrative embodiments, cochlear access device 200 comprises a hollow tubular structure that is configured to be implanted under the skin of a recipient in the recipient's mastoid bone 119 (FIG. 1). Specifically, when implanted, cochlear access device 200 has one end below skin 117 (FIG. 1), and an opposing distal end positioned in cochlea 116 (FIG. 116), thereby bypassing the recipient's outer 101 (FIG. 1) and middle 105 (FIG. 1) ears.

In the illustrative embodiments of FIG. 2A, the hollow tubular structure of cochlear access device 200 comprises a first portion 202 and a second portion 204. First portion 202 has a frustoconical shape and is referred to herein as frustoconical member 202. Second portion 204 has a cylindrical shape and is referred to as cylindrical member 204. The center points of frustoconical member 202 and cylindrical member 204 are positioned along a longitudinal axis 213 extending through cochlear access device 200. In the illustrative embodiments, first portion 202 has an average diameter which exceeds the average diameter of second portion 204.

As shown, frustoconical member 202 is a hollow circular frustum having circular bases or ends, shown as first end 206 and second end 208. First end 206 has a diameter which is larger than the diameter of second end 208. Following implantation, first end 206 is configured to be adjacent skin 117 of the recipient, while second end 208 is coupled to cylindrical member 204. Furthermore, first end 206 has an aperture 214 therein having its geometric center at longitudinal axis 213. Similarly, second end 208 has an aperture 217 which also has its geometric center at longitudinal axis 213.

Cylindrical member 204 is an elongate hollow element having a proximal end 210 and a distal end 212. Proximal end 210 is coupled to second end 208 of frustoconical member 202 such that the proximal end is connected to the edges of aperture 217. In other words, proximal end 210 of cylindrical member 204 is coupled to second end 208 such that the interiors of members 202 and 204 comprise a contiguous hollow portion 218. Cylindrical member 204 terminates in distal end 212 which, as noted above, is configured to be positioned in cochlea 116. Distal end 212 also has an aperture 216 therein which, similar to the apertures discussed above, having its geometric center positioned at longitudinal axis 213.

In certain embodiments of the present invention, cochlear access device 200 comprises a rigid structure manufactured from, for example, titanium. In other embodiments, cochlear access device is a resiliently flexible structure manufactured from, for example, a biocompatible elastic polymer.

In embodiments of the present invention, frustoconical member 202 and cylindrical member 204 comprise an integrated unitary device. In other embodiments, members 202 and 204 may be detachable from one another to permit connection of various sized and dimensioned members to one another.

As should be appreciated by one of ordinary skill in the art, the shape of cochlear access device 200 discussed above is provided for illustrative purposes only, and other shapes of members 202 and 204 may be utilized in other embodiments of the present invention.

In accordance with embodiments of the present invention, cochlear access device 200 may be implanted using a procedure which is similar to the procedure used to implant a cochlear implant. More specifically, to implant cochlear access device 200, a surgeon accesses mastoid bone 119 behind the recipient's ear. The surgeon then drills a passage from the surface of the mastoid through the mastoid to the middle ear. The shape of this passage roughly corresponds to the shape of frustoconical member 202. Cochlear access device 200 is inserted into this passage and distal end 212 is inserted into cochlea 116 through the round window, oval window, or through an artificial opening in the cochlea, commonly referred to as a cochleostomy. For ease of illustration, embodiments of the present invention will be discussed primarily herein with reference to implantation of distal end 212 inside cochlea 116. However, it should be appreciated that cochlear access device 200 may also positioned such that distal end 212 is adjacent, abutting or in physical contact with the exterior of cochlea 116. For example, distal end 212 may contact the round window or the oval window or any suitable external area of the cochlea. Once distal end 212 is positioned within cochlea 116, the skin 117 of the recipient may be positioned over first end 206.

As noted above, a cochlear access device in accordance with embodiments of the present invention may operate as a component of an implantable hearing system. In such embodiments, the cochlear access device is configured to have components of a hearing prosthesis positioned. FIGS. 3A-3C are cross-sectional views of a cochlear access device 300 in accordance with embodiments of the present invention having components of hearing prostheses 350 therein. In these embodiments, cochlear access device 300 and hearing prosthesis 350 are collectively referred to as an implantable hearing system. In the illustrative embodiments of FIGS. 3A-3C, hearing prostheses 350 are configured to mechanically stimulate the recipient's cochlea. In certain embodiments, hearing prostheses 350 utilized in the embodiments of FIGS. 3A-3C cause mechanical motion of the fluid within the cochlea using only components that do not require electrical power or electrical signals to operate. In such embodiments the hearing prostheses are entirely passive devices. In alternative embodiments, the hearing prosthesis 350 may include one or more components which require electrical power or electrical signals to operate.

Cochlear access device 300 illustrated in FIGS. 3A-3C is similar to cochlear access device 200 described above with reference to FIGS. 2A-2B. Specifically, cochlear access device 300 comprises a hollow tubular structure that is configured to be implanted under the skin of a recipient in the recipient's mastoid bone 119 (FIG. 1). When implanted, cochlear access device 300 has one end immediately below skin 117 (FIG. 1), and an opposing distal end positioned in cochlea 116 (FIG. 116).

The hollow tubular structure of cochlear access device 300 comprises a first portion 302 having a frustoconical shape, referred to herein as frustoconical member 302, and a second portion 304 having a cylindrical shape, referred to herein as cylindrical member 304. The center points of frustoconical member 302 and cylindrical member 304 are positioned along a longitudinal axis 313 extending through cochlear access device 300.

Similar to frustoconical member 202, member 302 is a frustum shaped member having circular bases or ends shown as first end 306 and second end 308. First end 306 has a diameter which is larger than the diameter of second end 308. Following implantation of cochlear access device 300, first end 306 is configured to be adjacent skin 117 of the recipient, while second end 308 is coupled to cylindrical member 304. Furthermore, first end 306 has an aperture 314 therein having its geometric center at longitudinal axis 313. Similarly, second end 308 has an aperture 317 which also has its geometric center at longitudinal axis 313.

Similar to cylindrical member 204, member 304 is an elongate hollow element having a proximal end 310 and a distal end 312. Proximal end 310 is coupled to second end 308 of frustoconical member 302 such that the proximal end is connected to the edges of aperture 317. In other words, proximal end 310 is coupled to second end 308 such that the interiors of members 302 and 304 comprise a contiguous hollow portion 318. Cylindrical member 304 terminates in a distal end 312 which, following implantation of cochlear access device 300, is positioned in cochlea 116. Distal end 312 also has an aperture 316 therein which, similar to the apertures discussed above, has its geometric center positioned at longitudinal axis 313.

FIG. 3A illustrates an exemplary implantable hearing system 390A comprising a hearing prosthesis 350A and cochlear access device 300A. In the illustrative embodiment, hearing prosthesis 350A comprises a first membrane 320 extending across aperture 314, and a second membrane 330 extending across aperture 316. As noted above, when cochlear access device 300A is implanted, first end 306 and thus membrane 320 are adjacent skin 117. As such, an acoustic sound signal which is presented to the recipient will travel through skin 117 to membrane 320. Membrane 320 is formed from a material that will vibrate when exposed to such a sound signal. The vibration of membrane 320 is transferred through hollow portion 318 of cochlear access device 300 to membrane 330, thereby causing corresponding vibration of membrane 330.

Because distal end 312, and thus membrane 330 are positioned inside cochlea 116, vibration of membrane 330 causes motion of the cochlea perilymph. Specifically, the vibration of membrane 330 causes a propagating wave within the perilymph. As should be appreciated by one of ordinary skill in the art, such a propagating wave excites the cochlear hair cells and evokes a hearing response by the recipient.

As should be appreciated by one of ordinary skill in the art, the material and/or elastic properties of a membrane determine the resulting vibration when a wave, such as a sound signal, is presented thereto. In embodiments of the present invention, the material and/or elastic properties of membranes 320, 330 are selected such that membrane 330 causes motion of the perilymph which results in a perception of the sound signal presented to membrane 320. In certain embodiments, the frustoconical shape of frustoconical member 302 in combination with the cylindrical shape of cylindrical member 304 enhances this perception by amplifying the vibration of membrane 320.

As discussed above, distal end 312 may be inserted into cochlea 116 at a variety of locations. For example, distal end 312 may be inserted through oval window 112 (FIG. 1), round window 121 (FIG. 1), a cochleostomy in cochlea 116 near semicircular canals 113 (FIG. 1) or another location. In certain embodiments, the entry location of distal end 312 should be sealed to prevent the egress of perilymph there from. In such embodiments, cochlear access device 300A includes a sealing member 326 which, when cochlear access device 300A is fully implanted, is positioned adjacent to the cochlea entry location to prevent the egress of perilymph from cochlea 116. In certain embodiments, sealing member 326 comprises a material which is configured to remain physically separate from cochlea 116. In other embodiments, sealing member 326 comprises a material or coating, such as a hydroxylapatite coating, which promotes integration with cochlea 116 or the bony structure surrounding the cochlea.

FIG. 3B illustrates an exemplary implantable hearing system 390B comprising hearing prosthesis 350B and cochlear access device 300B. In the illustrative embodiment, hearing prosthesis 350B comprises a first membrane 320 extending across aperture 314. Similar to hearing prosthesis 350A described above, membrane 320 is formed from a material that will vibrate when exposed to a sound signal received through skin 117.

In the illustrative embodiments of FIG. 3B, aperture 316 does not have a membrane disposed across thereof. As such, when distal end 312 is positioned inside cochlea 116, perilymph from cochlea 116 will enter cochlear access device 316 and remain in fluidic communication with the perilymph remaining inside cochlea 116. As such, vibration of membrane 320 sets up a propagating wave which is transferred to the perilymph within cochlea 116, thereby exciting the cochlear hair cells and evoking a hearing response by the recipient. In certain embodiments of the present invention, cochlear access device 300 is shaped or positioned such that hollow portion 318 is entirely filled with the perilymph.

As noted above, the material and/or elastic properties of membrane 320 determine the resulting vibration when a sound signal is presented thereto. In embodiments of the present invention, the material and/or elastic properties of membrane 320 are selected such that membrane 320 causes motion of the perilymph which results in a perception of the sound signal presented to the membrane.

Similar to the embodiment of FIG. 3A, cochlear access device 300B includes a sealing member 326 which, when the cochlear access device is fully implanted, is positioned adjacent to the cochlea entry location to prevent the egress of perilymph from cochlea 116. However, as noted above, sealing member 326 permits perilymph to flow into and out of cochlear access device 300B.

FIG. 3C illustrates a implantable hearing system 390C which comprises a hearing prosthesis 350C and a cochlear access device 300C. In the illustrative embodiment, hearing prosthesis 350C comprises a first membrane 320 extending across aperture 314. Similar to hearing prosthesis 350A described above, membrane 320 is formed from a material that will vibrate when exposed to a sound signal received through skin 117.

As shown, hearing prosthesis 350C further comprises a mechanical coupling element coupled to membrane 320. In the illustrative embodiment, mechanical coupling element 340 is an elongate rod 340 which extends from the geometric center of membrane 320 along longitudinal axis 313. Disposed at the distal end of rod 340 is an element 338 which functions as an artificial stapes. Specifically, when cochlear access device 300C is fully implanted, distal end 312, and thus element 338, are positioned inside cochlea 116. Because element 338 is mechanically coupled to membrane 330, vibration of membrane 330 causes longitudinal motion of element 338. Such motion of element 338 results in the generation of a propagating wave within the perilymph. Therefore, element 338 acts as an artificial stapes and, as such, is referred to herein as stapes prosthesis 338.

As noted above, the material and/or elastic properties of membrane 320 determine the resulting vibration when a sound signal is presented thereto. In embodiments of the present invention, the material and/or elastic properties of membrane 320 are selected such that membrane 320 causes motion of stapes prosthesis 338, and thus of the perilymph, resulting in a hearing perception of the sound signal presented to membrane 320.

Although FIG. 3C has been discussed with reference to use of a rod 340, it should be appreciated that other mechanical couplings may be used to couple membrane 320 to stapes prosthesis 338. For example, in certain embodiments, a mechanical coupling which amplifies the vibration of membrane 320 may be used. One such mechanical coupling element would comprise a spring-loaded member.

Similar to the embodiment described above, cochlear access device 300C includes a sealing member 326 which, when the cochlear access device is fully implanted, is positioned adjacent to the cochlea entry location to prevent the egress of perilymph from cochlea 116. In the illustrative embodiments of FIG. 3C, sealing member 326 is configured to permit movement of rod 340 while maintaining the seal.

As noted above, in certain embodiments of FIGS. 3A-3C, the shape of cochlear access device amplifies the vibration of membrane 320. In certain embodiments of the present invention, a hearing prosthesis 350 may comprise one or more additional elements which increase or amplify the vibration of membrane 320.

For example, in one such embodiment a piezoelectric disk may be positioned on membrane 320. As should be appreciated by one of ordinary skill in the art, a piezoelectric disk bends or deforms in response to an electrical signal. In one embodiment, when a sound signal is received at membrane 320, an electrical signal would be concurrently delivered to the piezoelectric disk, thereby increasing the vibration of the membrane. In certain embodiments, the electrical signal may be delivered by a sound input element such as a microphone.

FIGS. 4A and 4B are cross-sectional views of implantable hearing systems 490 each comprising a cochlear access device 400 and a hearing prosthesis 450. In the illustrative embodiments of FIGS. 4A and 4B, hearing prostheses 450 are active devices configured to mechanically stimulate the recipient's cochlea. That is, hearing prostheses 450 utilized in the embodiments of FIGS. 4A and 4B cause mechanical motion of the fluid within the cochlea using one or more components that require electrical power to operate.

Cochlear access device 400 illustrated in FIGS. 4A and 4B is similar to cochlear access device 200 described above with reference to FIGS. 2A-2B. Specifically, cochlear access device 400 comprises a hollow tubular structure that is configured to be implanted under the skin of a recipient in the recipient's mastoid bone 119 (FIG. 1). When implanted, cochlear access device 400 has one end immediately below skin 117 (FIG. 1), and an opposing end positioned in cochlea 116 (FIG. 116).

The hollow tubular structure of cochlear access device 400 comprises a first portion 402 having a frustoconical shape, referred to herein as frustoconical member 402, and a second portion 404 having a cylindrical shape, referred to herein as cylindrical member 404. The center points of frustoconical member 402 and cylindrical member 404 are positioned along a longitudinal axis 413 extending through cochlear access device 400.

Similar to frustoconical member 202, member 402 is a frustum shaped member having circular bases or ends shown as first end 406 and second end 408. First end 406 has a diameter which is larger than the diameter of second end 408. Following implantation of cochlear access device 400, first end 406 is configured to be adjacent skin 117 of the recipient, while second end 408 is coupled to cylindrical member 404. Furthermore, first end 406 has an aperture 414 therein having its geometric center at longitudinal axis 413. Similarly, second end 408 has an aperture 417 which also has its geometric center at longitudinal axis 413.

Similar to cylindrical member 204, member 404 is an elongate hollow element having a proximal end 410 and a distal end 412. Proximal end 410 is coupled to second end 408 of frustoconical member 402 such that the proximal end is connected to the edges of aperture 417. In other words, proximal end 410 is coupled to second end 408 such that the interiors of members 402 and 404 comprise a contiguous hollow portion 418. Cylindrical member 404 terminates in a distal end 412 which, following implantation of cochlear access device 400, is positioned in cochlea 116. Distal end 412 also has an aperture 416 therein which, similar to the apertures discussed above, has its geometric center positioned at longitudinal axis 413.

FIG. 4A illustrates an implantable hearing system 490A comprising a hearing prosthesis 450A and a cochlear access device 400A. In the illustrative embodiment, hearing prosthesis 450A comprises a transducer module 452A, a coupling member 440, and a stapes prosthesis 438. In the illustrative embodiment, transducer module 452A is coupled to first end 406 of frustoconical member 402. More specifically, transducer module 452A is configured to be removably mounted in aperture 414. As should be appreciated by on of ordinary skill in the art, a variety of mechanisms may be used to mounted transducer module 452A in aperture 414 and the details of such mounting will not be described in detail herein.

As shown, transducer module 452A includes an electrically operable transducer 454A which converts an electrical signal into a mechanical force. As would be appreciated, various types of transducer which convert electrical signals to mechanical force may be used in accordance with embodiments of the present invention. In certain embodiments, transducer 454A is a piezoelectric transducer.

In the embodiments of FIG. 4A, extending from transducer 454A is a mechanical coupling element 440. In the illustrative embodiment, mechanical coupling element 440 is an elongate rod which extends from transducer 454A along longitudinal axis 413. Disposed at the distal end of rod 440 is a stapes prosthesis 438. Similar to embodiments described above, when cochlear access device 400A is fully implanted, distal end 412, and thus stapes prosthesis 438, are positioned inside cochlea 116.

As described in greater detail below with reference to FIGS. 5-6, during operation of hearing prosthesis 450A, a sound signal is presented to the recipient of the prosthesis. The prosthesis includes one or more components (not shown) which receive and process the sound signal. These components generate an electrical signal representing the processed sound signal. This electrical signal is provided to transducer 454A. Transducer 454A converts the electrical signal into a longitudinal force which is exerted on rod 440. The force on rod 440 causes longitudinal motion of the rod and of stapes prosthesis 438. Such motion of stapes prosthesis 438 results in the generation of a propagating wave within the perilymph that provides the recipient with the ability to perceive the sound signal presented to the recipient.

Cochlear access device 400A includes a sealing member 426 which, when the cochlear access device is fully implanted, is positioned adjacent to the cochlea entry location to prevent the egress of perilymph from cochlea 116. In the illustrative embodiments of FIG. 4A, sealing member 426 is configured to permit movement of rod 440 while maintaining the seal.

FIG. 4B illustrates a implantable hearing system 490B comprising a hearing prosthesis 450B and a cochlear access device 400B. In the illustrative embodiment, hearing prosthesis 450B comprises a transducer module 452B and an excitation element 444. In the illustrative embodiment, transducer module 452B is coupled to first end 406 of frustoconical member 402 in substantially the same manner as discussed above with reference transducer module 452A.

In the illustrative embodiments of FIG. 4A, when distal end 412 is positioned inside cochlea 116, perilymph from cochlea 116 will enter cochlear access device 400B through aperture 416. In certain embodiments of the present invention, cochlear access device 400B is shaped or positioned such that hollow portion 418 is entirely filled with the perilymph.

As described in greater detail below with reference to FIGS. 5-6, during operation of hearing prosthesis 450B, a sound signal is presented to the recipient of the prosthesis. The prosthesis includes one or more components (not shown) which receive and process the sound signal. These components then generate an electrical signal representing the processed sound signal. This electrical signal is provided to a transducer 454B within transducer module 452B. Transducer 454B converts the electrical signal into lateral motion of excitation element 444. In other words, transducer 454B causes motion of distal end 419 of excitation element 444 which is orthogonal to longitudinal axis 413. This motion is illustrated in FIG. 4B by arrows 456.

As discussed above, because perilymph enters cochlear access device 400 through aperture 416, excitation element 444 is in contact with the perilymph. As such, the lateral motion of distal end 419 results in the generation of a propagating wave within the perilymph that is transferred to cochlea 116, thereby providing the recipient with the ability to perceive the sound signal presented to the recipient.

Figure 5:
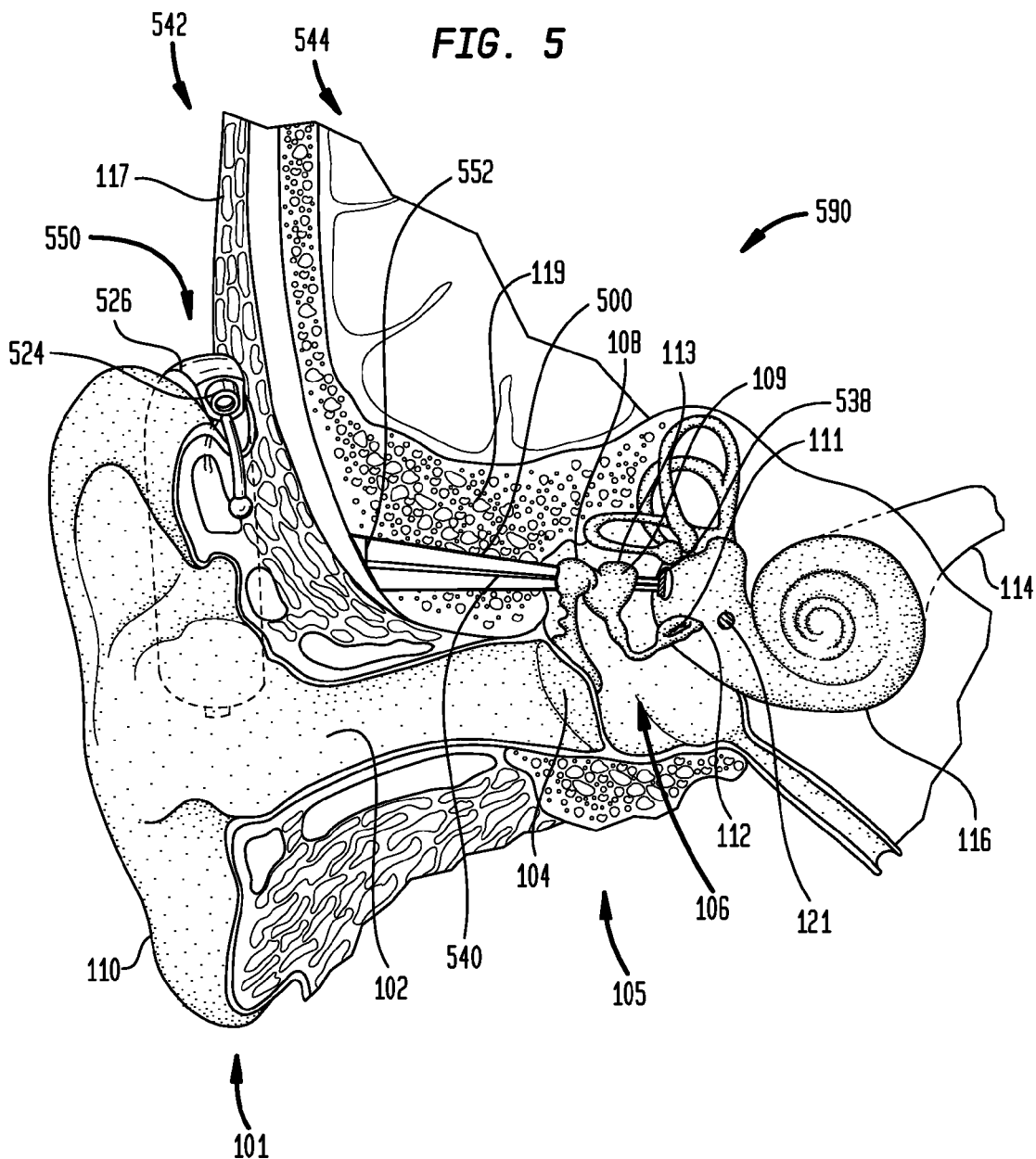
FIG. 5 is a perspective view of an implantable hearing system implanted in a recipient, in accordance with embodiments of the present invention.

FIG. 5 is a partial cross-sectional view of a recipient's head illustrating an implantable hearing system 590. Implantable hearing system 590 comprises a cochlear access device 500, and a hearing prosthesis 550. In the illustrative embodiment, hearing prosthesis 550 comprises an external component 542 which is directly or indirectly attached to the body of the recipient, and an internal component 544 which is temporarily or permanently implanted in the recipient. External component 542 typically comprises one or more sound input elements, such as microphone 524 for detecting sound, a sound processing unit 526, a power source (not shown), and an external transmitter unit (not shown). The external transmitter unit and the components thereof have been omitted for ease of illustration.

As discussed below with reference to FIG. 6, external transmitter unit typically comprises an external coil (not shown) and, preferably, a magnet (not shown) secured directly or indirectly to the external coil. Sound processing unit 526 processes the output of microphone 524 that is positioned, in the depicted embodiment, by auricle 110 of the recipient. Sound processing unit 526 generates encoded signals, sometimes referred to herein as encoded data signals, which are provided to external transmitter unit via, for example, a cable (not shown).

Internal component 544 comprises a transducer module 552 coupled to cochlear access device 500 extending through mastoid bone 119 of the recipient. Cochlear access device 500 is substantially similar to the access devices described above with reference to FIGS. 2A-2B and will not be described in greater detail herein.

As described below with reference to FIG. 6, transducer module 552 comprises an internal receiver unit (not shown) and a transducer (not shown) which have been omitted in FIG. 5 for ease of illustration. Internal receiver unit comprises an internal coil (not shown), and preferably, a magnet (also not shown) fixed relative to the internal coil. Internal receiver unit and the transducer are hermetically sealed within a biocompatible housing. In the illustrative embodiments, the internal coil receives power and encoded signals from external coil.

Coupled to transducer module 552 is rod 540 having stapes prosthesis 538 disposed at a distal end thereof. The transducer uses the power and encoded signals received by internal coil to generate longitudinal motion of stapes prosthesis 538. As described above with reference to FIG. 4A, the longitudinal movement of stapes prosthesis evokes a hearing percept by the recipient.

Figure 6:
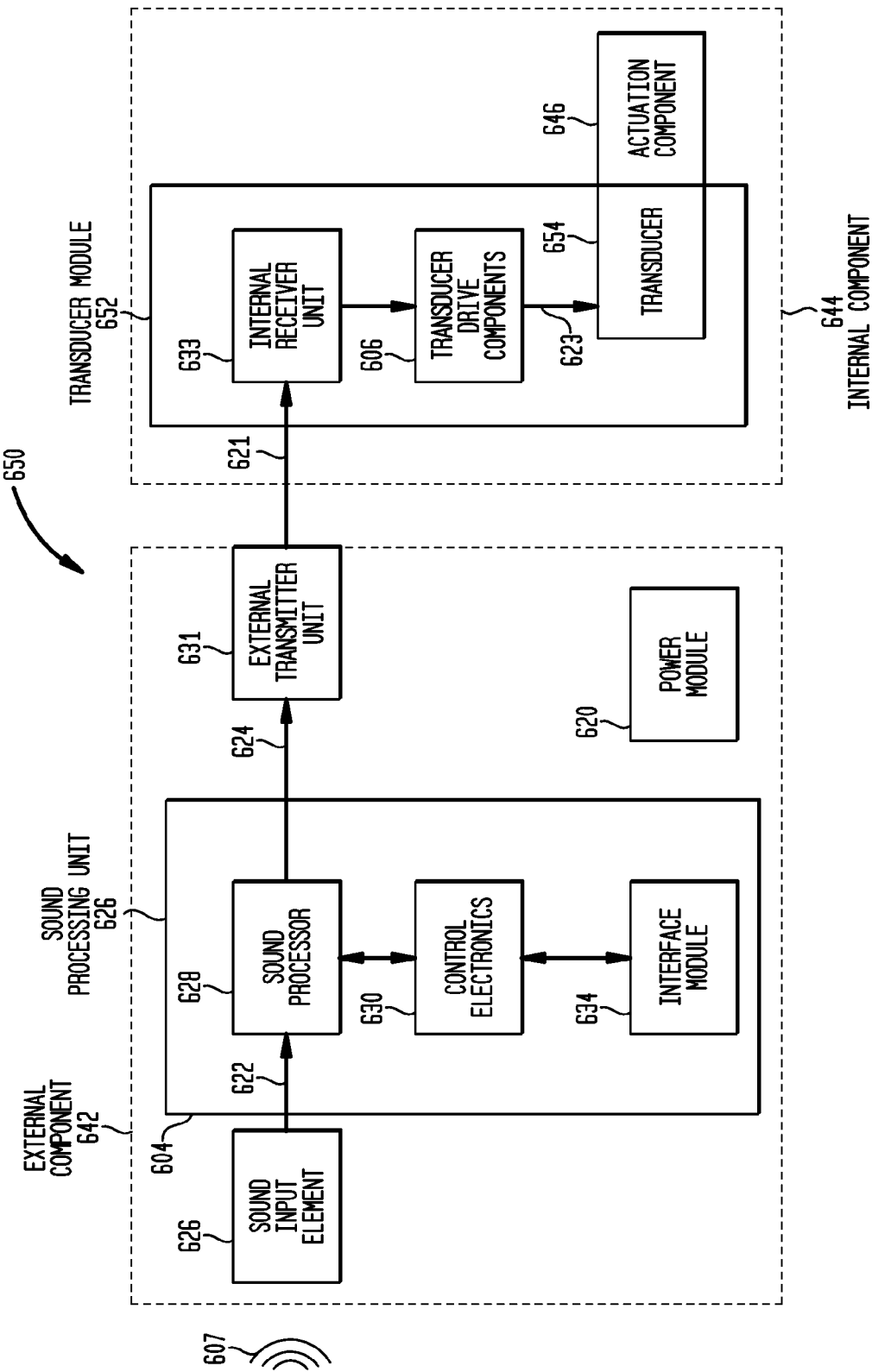
FIG. 6 is a perspective view of an implantable hearing system implanted in a recipient, in accordance with embodiments of the present invention.

FIG. 6 is a functional block diagram of a hearing prosthesis 650 which may be implemented with a cochlear access device (not shown) in accordance with embodiments of the present invention. As shown, hearing prosthesis 650 comprises external component 642 and an internal component 644. External component 542 comprises one or more sound input elements 624, a sound processing unit 626, a power source 620, and an external transmitter unit 631.

Sound input element 624 receives a sound 607 and outputs an electrical signal 622 representing the sound to a sound processor 628 in sound processing unit 626. Sound processor 628 generates encoded signals 624 which are provided to external transmitter unit 631. As should be appreciated, sound processor 628 uses one or more of a plurality of techniques to selectively process, amplify and/or filter electrical signal 622 to generate encoded signals 624. In certain embodiments, sound processor 628 may comprise substantially the same sound processor as is used in an air conduction hearing aid. In further embodiments, sound processor 628 comprises a digital signal processor.

External transmitter unit 631 is configured to transmit the encoded data signals to internal component 644. In certain embodiments, external transmitter unit 631 comprises an external coil which forms part of a radio frequency (RF) link with components of internal component 644.

Internal component 644 comprises a transducer module 652 which is implanted in a cochlear access device in accordance with embodiments of the present invention. Transducer module 652 comprises an internal receiver unit 633, transducer drive components 606, and transducer 654. Internal receiver unit 633 comprises an internal coil which receives power and encoded signals from the external coil in external transmitter unit 631.

The encoded signals 621 received by internal receiver unit 633 are provided to transducer drive components 606. Based on the received signals, transducer drive components 606 output an electrical drive signal 623 to transducer 654. Based on drive signal 623, transducer 654 actuates component 646 to cause a propagating wave in the perilymph of the recipient's cochlea. Component 646 may comprise a rod and stapes prosthesis as described above with reference to FIG. 4A, or an excitation element as described above with reference to FIG. 4B.

As shown in FIG. 6, sound processing unit 626 further comprises an interface module 634 and control electronics 630. These components may function together to permit a recipient or other user of hearing prosthesis 650 to control or alter the operation of the prosthesis. For example, in certain embodiments of the present invention, based on inputs received by an interface module 634, control electronics 630 may provide instructions to, or request information from, other components of prosthesis 650.

Although the embodiments of FIG. 6 have been described with reference to an external component, it should be appreciated that in alternative embodiments hearing prosthesis 650 is a totally implantable prosthesis. In such embodiments, sound processing unit 626 is implanted in a recipient in a cochlear access device in accordance with embodiments of the present invention. In such embodiments, sound processor may communicate directly with the transducer drive components and the transmitter and receiver may be eliminated.

Figure 7:
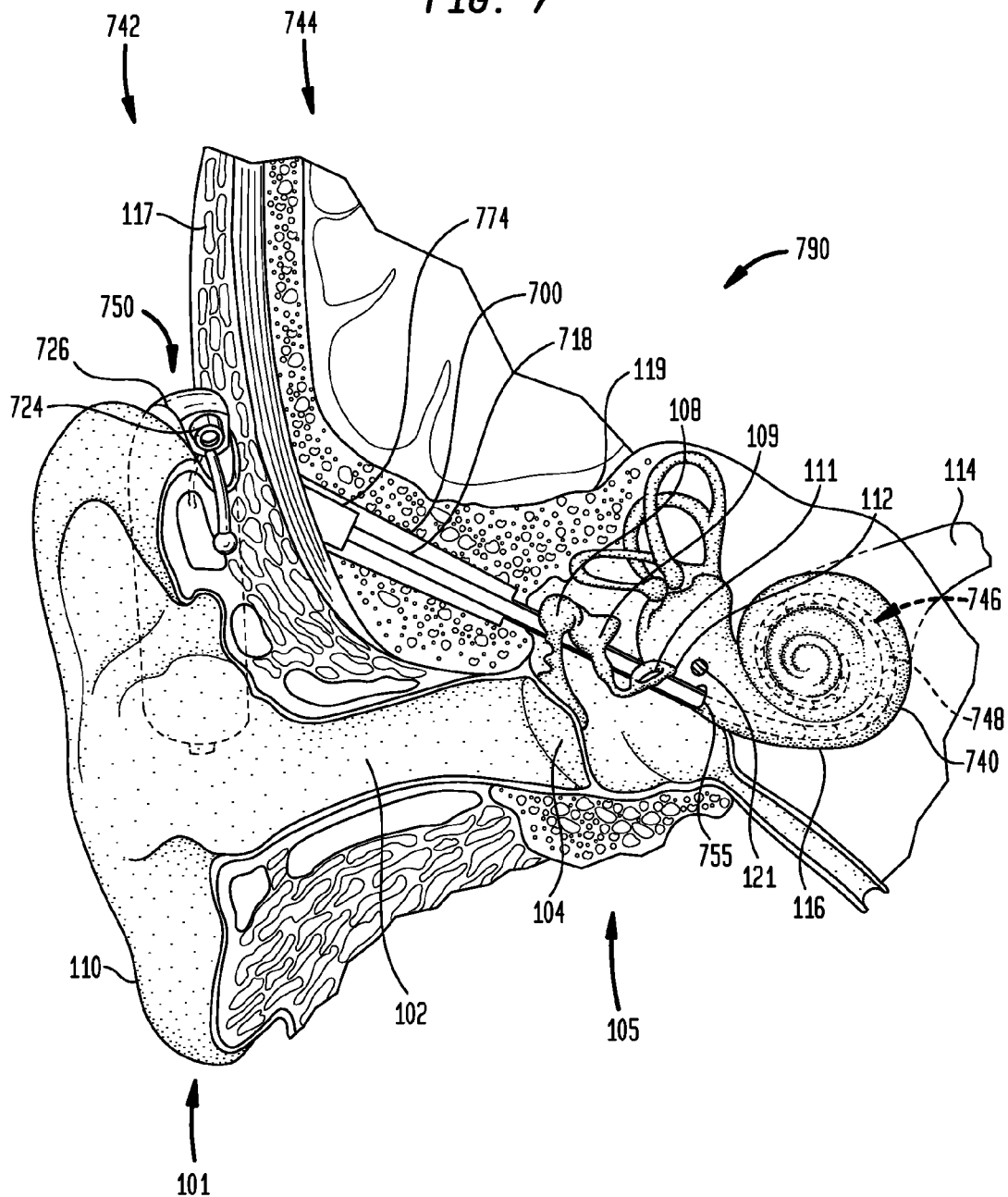
FIG. 7 is a partial cross-sectional view of a recipient's head illustrating a cochlear access device having elements of a cochlear implant positioned therein, in accordance with embodiments of the present invention.

As noted above, a cochlear access device in accordance with embodiments of the present invention may be used with hearing prosthesis configured to electrically stimulate the recipient's cochlea. One such hearing prosthesis is a cochlear implant. FIG. 7 is a partial cross-sectional view of a recipient's head illustrating an implantable hearing system 790 comprising a cochlear access device 700 and a cochlear implant 750. As described in greater detail below, components of cochlear implant 750 extend through cochlear access device 700.

In the embodiment of FIG. 7, cochlear access device 700 is similar to the cochlear access device described above with reference FIGS. 2A and 2B. Specifically, cochlear access device 700 comprises a hollow tubular structure that is configured to be implanted under the skin 117 of a recipient in the recipient's mastoid bone 119. When implanted, cochlear access device 700 has one end immediately below skin 117, and an opposing end positioned in cochlea 116, thereby bypassing the recipient's outer 101 and middle 105 ears. The details of exemplary cochlear access devices have been described above and will not be repeated with reference to FIG. 7

In the embodiments of FIG. 7, cochlear implant 750 comprises an external component 742 which is directly or indirectly attached to the body of the recipient, and an internal component 744 which is temporarily or permanently implanted in the recipient. As shown in FIG. 7, elements of internal component 744 are positioned in cochlear access device 700.

External component 742 comprises one or more sound input elements, such as microphone 724 for detecting sound, a sound processing unit 726, a power source (not shown), and an external transmitter unit (not shown). External transmitter unit and the components thereof have not been shown in FIG. 7 for ease of illustration.

External transmitter unit comprises an external coil (not shown) and, preferably, a magnet (not shown) secured directly or indirectly to the external coil. Sound processing unit 726 processes the output of microphone 724 that is positioned, in the depicted embodiment, by auricle 110 of the recipient. Sound processing unit 126 generates encoded signals, sometimes referred to herein as encoded data signals, which are provided to the external transmitter unit.

Internal component 744 comprises an internal receiver/stimulator unit 774 and an elongate electrode assembly 718 positioned in cochlear access device 700. Receiver/stimulator unit 774 comprises an internal coil (not shown), and preferably, a magnet (also not shown) fixed relative to the internal coil. The internal coil receives power and stimulation data from the external coil via a radio frequency (RF) link.

Elongate electrode assembly 718 has a proximal end connected to receiver/stimulator unit 774, and a distal end implanted in cochlea 116. Electrode assembly 718 extends from receiver/stimulator unit 774 to cochlea 116 through cochlear access device 700. In certain circumstances, electrode assembly 718 may be inserted into cochlea 116 via a cochleostomy 755. In other circumstances, electrode assembly 718 may be inserted through round window 121 or oval window 112.

Electrode assembly 718 comprises a longitudinally aligned and distally extending array 746 of electrodes 748, sometimes referred to as electrode array 746 herein, disposed along a length thereof. Although electrode array 746 may be disposed on electrode assembly 718, in most practical applications, electrode array 746 is integrated into electrode assembly 718. As such, electrode array 746 is referred to herein as being disposed in electrode assembly 718. Receiver/stimulator unit 774 generates stimulation signals which are applied by electrodes 748 to cochlea 116, thereby stimulating auditory nerve 114.

Although the embodiments of FIG. 7 have been described with reference to an external component, it should be appreciated that in alternative embodiments cochlear implant 750 is a totally implantable cochlear implant. In such embodiments, sound processing unit 726 and/or sound input element 724 are implanted in the recipient in cochlear access device 700.

Figure 8:
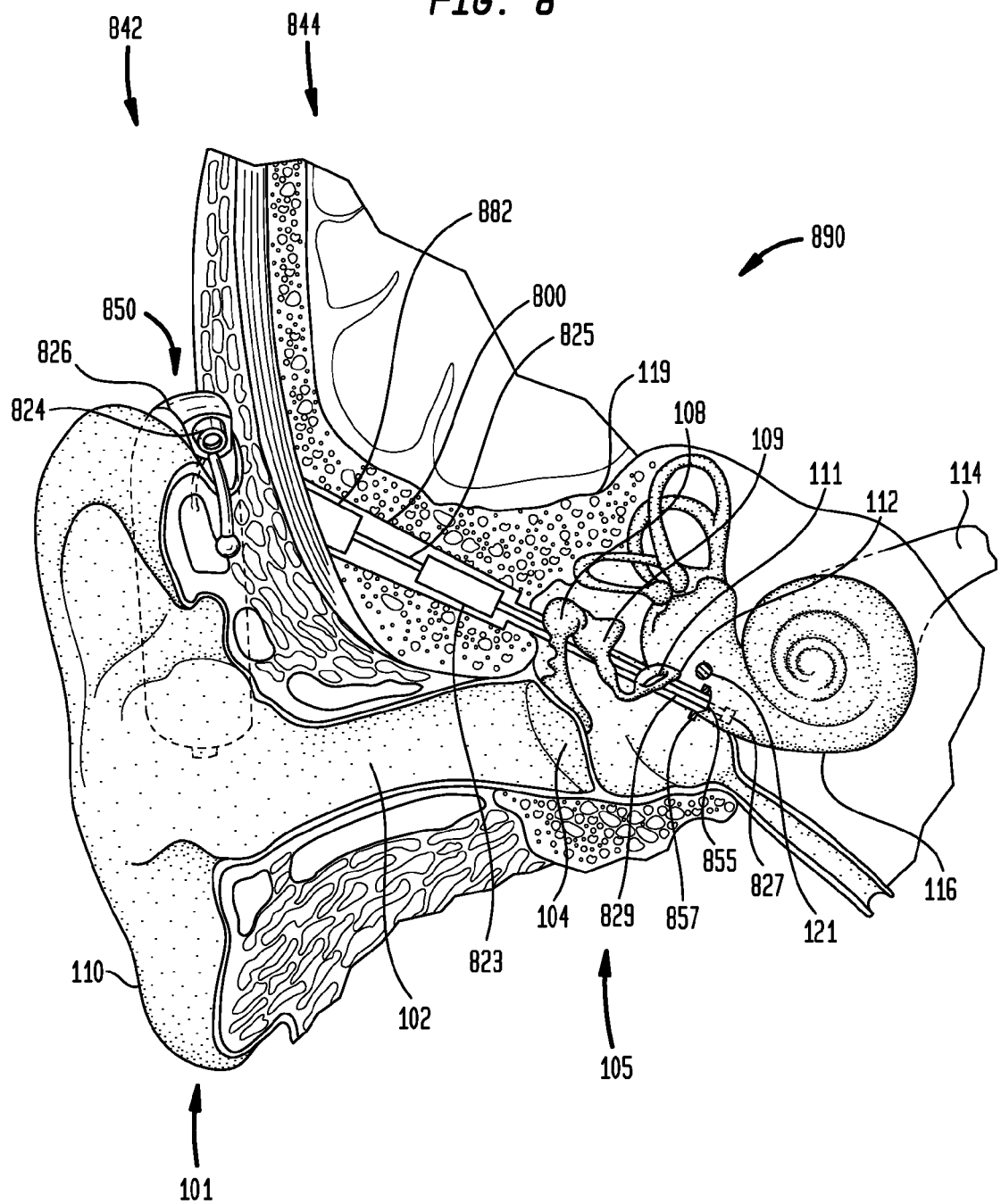
FIG. 8 is a partial cross-sectional view of a recipient's head illustrating the position of a cochlear access device having element of a direct acoustical cochlear stimulator therein, in accordance with embodiments of the present invention.

As noted above, a cochlear access device in accordance with embodiments of the present invention may be used with hearing prosthesis configured to mechanically stimulate the recipient's cochlea. Embodiments of such mechanically stimulating hearing prosthesis are described above with reference to FIGS. 3A-6. FIG. 8 is a partial cross-sectional view of a recipient's head illustrating an implantable hearing system 890 which comprises a cochlear access device 800 and a mechanically stimulating hearing prosthesis 850.

In the illustrative embodiment of FIG. 8, mechanically stimulating hearing prosthesis 850 comprises an external component 842 which is directly or indirectly attached to the body of the recipient, and an internal component 844 which is temporarily or permanently implanted in the recipient. As shown in FIG. 8, internal component 844 is positioned in cochlear access device 800.

External component 842 comprises one or more sound input elements, such as microphone 824 for detecting sound, a sound processing unit 826, a power source (not shown), and an external transmitter unit (not shown). The external transmitter unit and components thereof have not been shown in FIG. 8 for ease of illustration.

External transmitter unit comprises an external coil (not shown) and, preferably, a magnet (not shown) secured directly or indirectly to the external coil. Sound processing unit 826 processes the output of microphone 824 that is positioned, in the depicted embodiment, by auricle 110 of the recipient. Sound processing unit 826 generates encoded signals, sometimes referred to herein as encoded data signals, which are provided to the external transmitter unit.

Internal component 844 comprises an internal receiver unit 882 and a transducer module 823 each positioned in cochlear access device 800. Receiver unit 882 comprises an internal coil (not shown), and preferably, a magnet (also not shown) fixed relative to the internal coil. The internal coil receives power and stimulation data from the external coil via a radio frequency (RF) link.

In operation, encoded signals received by internal receiver unit 882 are relayed to transducer module 823 via signal line 825. Transducer module 823 includes a transducer (not shown) and transducer drive components (also not shown). The encoded signals are provided to transducer drive components, which based on the received signals, output an electrical drive signal to the transducer. Based on drive signal 623, transducer 654 generates longitudinal motion of a rod 829. Disposed on the end of rod 829 is a stapes prosthesis 827. Stapes prosthesis 827 comprises a resiliently flexible component which is configured to actuate in response to motion of rod 829. The actuation of stapes prosthesis 827 generates propagating waves in the perilymph of cochlea 116 which evoke hearing percepts by the recipient of the sound received at sound input element 824.

Unless otherwise noted above, it should be appreciated by one of ordinary skill in the art that the above described shapes of the cochlear access devices are merely illustrative. As such, in embodiments of the present invention, alternative shapes for the cochlear access devices may be used.

Further features and advantages of the present invention may be found in related to commonly owned and co-pending U.S. patent application entitled "IMPLANTABLE HEARING SYSTEM," filed concurrently herewith. This application is hereby incorporated by reference herein.

Although the present invention has been fully described in conjunction with several embodiments thereof with reference to the accompanying drawings, it is to be understood that various changes and modifications may be apparent to those skilled in the art. For example, it should be appreciated that embodiments described in the context of one aspect may be used in other aspects without departing from the scope of the present invention. Such changes and modifications are to be understood as included within the scope of the present invention as defined by the appended claims, unless they depart there from.

What is claimed is:

1. A system for rehabilitating the hearing of a recipient, the system comprising:
   an elongate hollow access device having a first end and a distal end, and configured to be at least partially positioned in the mastoid bone of the recipient, such that the first end is positioned adjacent the surface of the mastoid bone, and the distal end is inserted into the cochlea; and
   a hearing prosthesis configured to be at least partially implanted in the access device and configured to at least one of mechanically and electrically stimulate the recipient's cochlea, wherein the access device comprises:
      an elongate first portion having a first and a second end; and
      an elongate second portion having proximal and distal ends, wherein the proximal end of the second portion is coupled to the second end of the first portion.

2. The system of claim 1, wherein the access device has a symmetrical shape about a longitudinal axis through the center of the device, and comprises:
   a first end having an aperture with its geometric center positioned at the longitudinal axis; and
   a distal end having an aperture with its geometric center positioned at the longitudinal axis.

3. The system of claim 1, wherein the average diameter of the first portion is greater than the average diameter of the second portion.

4. The system of claim 1, wherein the proximal end of the second portion is detachably coupled to the second end of the first portion.

5. The system of claim 1, wherein the first portion has a frustoconical shape, and wherein the second portion has an elongate cylindrical shape.

6. The system of claim 1, wherein the access device is rigid.

7. The system of claim 1, wherein the access device is resiliently flexible.

8. The system of claim 1, wherein the access device further comprises:
   a sealing member disposed at the distal end configured to prevent perilymph egress from the cochlea.

9. The system of claim 1, wherein the hearing prosthesis comprises a mechanical stimulator.

10. The system of claim 9, wherein the distal end of the access device is configured to permit the flow of perilymph into the device, and therein the mechanical stimulator comprises:
    a transducer disposed in the access device;
    an elongate excitation element extending from the transducer configured to be contact with the perilymph in the access device,
    wherein actuation of the transducer causes lateral movement of the element so as to generate motion of the perilymph.

11. The system of claim 1, wherein the hearing prosthesis is a cochlear implant.

12. A system for rehabilitating the hearing of a recipient, the system comprising:
    an elongate hollow access device having a first end and a distal end, and configured to be at least partially positioned in the mastoid bone of the recipient, such that the first end is positioned adjacent the surface of the mastoid bone, and the distal end is inserted into the cochlea; and
    a hearing prosthesis configured to be at least partially implanted in the access device and configured to at least one of mechanically and electrically stimulate the recipient's cochlea, wherein
    the hearing prosthesis comprises a mechanical stimulator, and
    the mechanical stimulator comprises:
       a transducer disposed in the access device;
       a stapes prosthesis positioned in the distal end of the access device in contact with the cochlea perilymph; and
       a mechanical coupling element connecting the transducer to the stapes prosthesis such that actuation of the transducer causes motion of the perilymph.

13. The system of claim 12, wherein the transducer is a piezoelectric transducer.

* * * * *